(12) United States Patent
Langen

(10) Patent No.: US 12,342,922 B2
(45) Date of Patent: Jul. 1, 2025

(54) METHOD FOR APPLYING A COSMETIC SUBSTANCE TO THE SKIN OF A PERSON

(71) Applicant: J. Wagner GmbH, Markdorf (DE)

(72) Inventor: Valentin Langen, Überlingen (DE)

( * ) Notice: Subject to any disclaimer, the term of this patent is extended or adjusted under 35 U.S.C. 154(b) by 0 days.

(21) Appl. No.: 18/614,137

(22) Filed: Mar. 22, 2024

(65) Prior Publication Data

US 2024/0306793 A1    Sep. 19, 2024

Related U.S. Application Data

(63) Continuation of application No. 17/288,490, filed as application No. PCT/EP2019/078958 on Oct. 23, 2019, now Pat. No. 11,944,179.

(30) Foreign Application Priority Data

Oct. 24, 2018  (DE) .......................... 102018126568.9

(51) Int. Cl.
*A45D 34/04*     (2006.01)
*A61M 35/00*    (2006.01)
(Continued)

(52) U.S. Cl.
CPC ............. *A45D 34/04* (2013.01); *A61M 35/00* (2013.01); *B05B 5/025* (2013.01); *B05B 5/16* (2013.01);
(Continued)

(58) Field of Classification Search
CPC .......... A45D 34/04; B05B 5/16; B05B 5/025; B05B 5/1691; B05B 12/12; B05B 12/004; B05B 12/126
See application file for complete search history.

(56) References Cited

U.S. PATENT DOCUMENTS

| 5,063,350 A | 11/1991 | Hemming et al. |
| 11,351,402 B2 | 6/2022 | Toko et al. |

(Continued)

FOREIGN PATENT DOCUMENTS

| CN | 106667431 A | 5/2017 |
| CN | 206296104 U | 7/2017 |

(Continued)

OTHER PUBLICATIONS

Foreign communication from the priority International Application No. PCT/EP2019/078958, International Search Report, 3 pages.
(Continued)

*Primary Examiner* — Jennifer C Chiang

(74) *Attorney, Agent, or Firm* — Scheef & Stone, L.L.P.; Keith C. Rawlins, Esq.

(57) ABSTRACT

A method for applying a cosmetic substance to the skin of a person, using a device for electrostatically spraying the cosmetic substance. The device has a container, a nozzle arrangement, a conveyor device, a high-voltage source, a processor for processing measurement values, data and/or reference values, a storage device and a transmitting and receiving unit for transmitting the measurement values, data and/or reference values to an external data processing device and/or for receiving further measurement values, data and/or reference values from the external data processing device.

26 Claims, 1 Drawing Sheet

(51) Int. Cl.
    *B05B 5/025*     (2006.01)
    *B05B 5/16*      (2006.01)
    *B05B 12/00*     (2018.01)
    *B05B 12/12*     (2006.01)

(52) U.S. Cl.
    CPC .......... *B05B 5/1691* (2013.01); *B05B 12/004* (2013.01); *B05B 12/12* (2013.01); *B05B 12/126* (2013.01)

(56) References Cited

U.S. PATENT DOCUMENTS

| 2016/0022011 A1 | 1/2016 | Rabe et al. |
| 2020/0114377 A1 | 4/2020 | Barthelmes et al. |
| 2020/0275758 A1 | 9/2020 | Miller et al. |

FOREIGN PATENT DOCUMENTS

| EP | 2612644 A1 | 7/2013 | | |
| EP | 3375323 A1 | 9/2018 | | |
| JP | 2008279322 A | 11/2008 | | |
| KR | 20080059157 A | 6/2008 | | |
| KR | 20170020912 A | 2/2017 | | |
| KR | 20180057721 A | 5/2018 | | |
| WO | WO-2008132848 A1 * | 11/2008 | ............. | A45D 44/00 |
| WO | 2018193068 A1 | 10/2018 | | |
| WO | 2019103974 A1 | 5/2019 | | |

OTHER PUBLICATIONS

Foreign communication from the priority International Application No. PCT/EP2019/078958, International Preliminary Report on Patentability, 8 pages.
Foreign communication from the priority International Application No. PCT/EP2019/078958, Written Opinion, 9 pages.
Foreign communication from the Chinese Patent Office, Office Action dated Apr. 25, 2022, 8 pages.
Foreign communication from the Japanese Patent Office, Office Action dated May 23, 2022, 4 pages.
Foreign communication from the South Korean Patent Office, Office Action dated Aug. 25, 2022, 15 pages.
Foreign communication from the European Patent Office, Office Action dated May 13, 2022, 8 pages.
Foreign communication from the German Patent Office, Office Action dated Aug. 20, 2019, 9 pages.

* cited by examiner

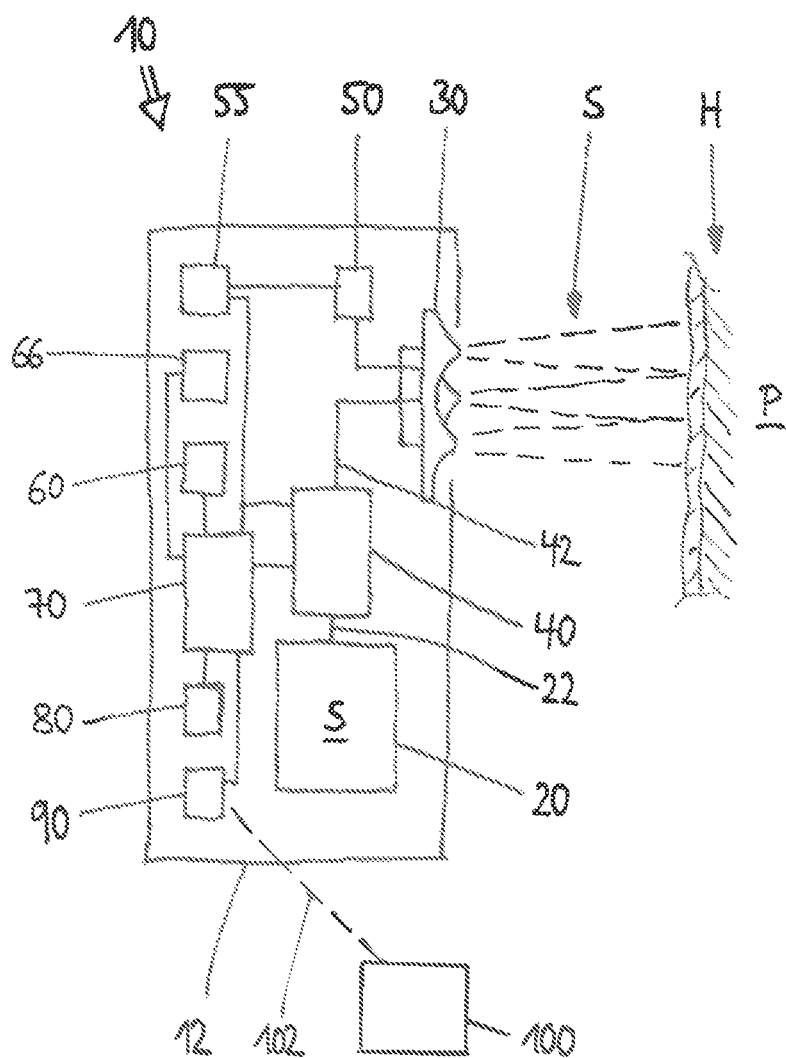

METHOD FOR APPLYING A COSMETIC SUBSTANCE TO THE SKIN OF A PERSON

CROSS-REFERENCE TO RELATED APPLICATIONS

This application is continuation of U.S. patent application Ser. No. 17/288,490, filed on Apr. 23, 2021, entitled "Method for Applying a Cosmetic Substance to the Skin of a Person," which is a filing under 35 U.S.C. 371 of International Application No. PCT/EP2019/078958, filed Oct. 23, 2019, entitled "Method for Applying a Cosmetic Substance to the Skin of a Person," which claims priority to German Patent Application No. 10 2018 126 568.9, filed Oct. 24, 2018, which applications are incorporated by reference herein in their entirety.

FIELD OF THE DISCLOSURE

The invention relates to a method for applying a cosmetic substance to the skin of a person according to the preamble of claim 1.

BACKGROUND

Cosmetic substances, such as e.g. skincare products, lotions, sunscreens, self-tanning creams and the like, are ordinarily applied to the skin of a person by hand. Such a method is—in particular if larger areas of skin need to be treated-time-consuming and a not inconsiderable part of the substance is lost in the hands.

To minimize contact with the cosmetic substance by the person applying it and to obtain an improved distribution of the substance, pump sprays or pressurized aerosol containers are offered for sale that contain the cosmetic substance and atomize and spray it using a propellant. A disadvantage of this, however, is that a large part of the substance goes not onto the skin but rather into the immediate surroundings, which is undesirable.

For more targeted application of a cosmetic substance to the skin of a person, spraying devices that provide for electrostatic atomization have also been designed. In this instance, the particles or droplets of the substance to be sprayed are electrically charged using a high-voltage electrode and are directed onto the skin of the person to be treated on the basis of electrical field forces, the skin being grounded with reference to the spraying device.

Within the context of the present invention, electrostatic atomization covers all atomization or nebulization processes that atomize or nebulize substances using effects of the action of a high voltage. In particular electrohydrodynamic effects and electrokinetic effects are also covered by the concept of this type of atomization. Within the context of the invention, an electrohydrodynamic atomization can also be regarded as an electrostatic atomization.

Electrostatic spraying devices of this kind have—as disclosed in WO 2002 055 211 A1, for example—a container for the product to be sprayed, a conveying apparatus, which usually has a drive in order to operate a piston inside the container or a feed pump, a nozzle for distributing the product and a high-voltage source with an associated high-voltage electrode, in order to electrostatically charge the substance or the particles and droplets thereof.

All of the cited methods of application have the disadvantage that the cosmetic substance is often applied to the skin unevenly. Application by hand can be dosed and controlled only inaccurately. The available spraying devices deliver the substance with a substantially constant output quantity, which-if the container is moved unevenly or oriented incorrectly relative to a section of skin-likewise leads to an uneven distribution of the substance. Consequently, areas on the skin arise in which too much, too little or even no substance has been applied. The substance therefore cannot work in optimum fashion, however, in particular if the correct dosage is important.

When applying cosmetic substances, in particular in the case of sun protection products, self-tanning creams, insect repellents, lotions and the like, material is moreover often—consciously or unconsciously—saved because the products are relatively expensive. In the case of substances that need to be applied repeatedly at regular intervals or to maintain a healing or protective action, adherence to repeated application is often forgotten. Individual adaptations when applying the cosmetic substance to the skin of a person are not possible.

SUMMARY

It is an aim of the invention to develop a method for applying a cosmetic substance to the skin of a person that overcomes the disadvantages of the prior art and allows a cosmetic substance to be applied as evenly as possible and in optimum fashion for the respective person. The method is furthermore supposed to be able to make individual adaptations and meet personal needs. It is intended to be of simple design and inexpensive to implement.

Main features of the invention are specified in claim 1. Refinements are the subject of claims 2 to 24.

As a solution, the invention proposes a method for applying a cosmetic substance to the skin of a person, the method being carried out using a device for electrostatically spraying the cosmetic substance.

The device has a container for the cosmetic substance, a nozzle arrangement for spraying the cosmetic substance, a conveying apparatus for conveying the cosmetic substance from the container to the nozzle arrangement, a high-voltage source, a processor for processing measured values, data and/or reference values, a memory for storing the measured values, data and/or reference values, a transmitting and receiving unit for transferring the measured values, data and/or reference values to an external data processing apparatus and/or for receiving further measured values, data and/or reference values from the external data processing apparatus.

The method comprises the following steps:
the measured values, further measured values, personal data of the person, further external data and/or reference values are captured and/or ascertained and transmitted to the processor,
the processor processes the measured values, the further measured values, the personal data, the further external data and/or the reference values to produce at least one result,
the processor takes the results as a basis for varying the output quantity of the cosmetic substance to be sprayed from the device.

It is thus possible to use the device to achieve a largely even application, which is optimum for the respective person, of the cosmetic substance. All areas of the skin to be treated can be coated completely and with an invariably sufficient and even quantity of cosmetic substance, as a result of which the substance can develop the desired or intended effect in optimum fashion. The method has a simple structure and can be implemented inexpensively using simple means.

The processor advantageously varies the output quantity of the cosmetic substance to be sprayed by regulating the conveying apparatus. Said conveying apparatus—in the form of a conveying pump—can be operated more quickly or more slowly, for example. If the conveying apparatus drives a piston in the container for the cosmetic substance, said piston can be moved more quickly or more slowly.

Additionally or alternatively, the processor can vary the output quantity of the cosmetic substance to be sprayed by regulating the high-voltage source. This could also allow the droplet size and distribution within the sprayed cosmetic substance to be adapted.

A further refinement of the method according to the invention provides for the processor to vary the output quantity of the cosmetic substance to be sprayed by influencing the nozzle arrangement. This can be effected for example by virtue of the nozzle cross section, the nozzle arrangement, the nozzle orientation or the number of engaged nozzles being altered.

A further improvement to application of the cosmetic substance is achieved by virtue of the output quantity of the cosmetic substance to be sprayed being varied on the basis of the results in real time. Changes in the measured values, the further measured values, the personal data of the person, the further external data and/or the reference values are taken into consideration immediately and the output quantity is adapted accordingly.

In a preferred embodiment, the device has at least one sensor, wherein the measured values are captured by the at least one sensor during application of the cosmetic substance to the skin of the person. This also allows the output quantity of cosmetic substance to be adapted for the individual circumstances and needs of the person using the device.

Expediently, the at least one sensor captures a speed, an acceleration, a deceleration and/or an inclination of the device.

By way of example, in one design of the invention, the output quantity of the cosmetic substance to be sprayed is varied on the basis of the speed of the device, wherein the output quantity of the cosmetic substance to be sprayed is increased when the speed rises and wherein the output quantity of the cosmetic substance to be sprayed is decreased when the speed falls.

The speed of movement of the spraying device is consequently captured by way of one or more installed sensors. The ascertained measured values are forwarded to the processor, which processes the measured values and calculates motion data. These motion data are taken as a basis for varying the optimum spray quantity, also for speed changes and preferably in real time.

In an alternative or additional refinement of the invention, the output quantity of the cosmetic substance to be sprayed is varied on the basis of an acceleration and/or a deceleration of the device. In this case, the output quantity of the cosmetic substance to be sprayed is increased for an acceleration of the device, whereas the output quantity of the cosmetic substance to be sprayed is decreased for a deceleration of the device.

In a further embodiment of the invention, the output quantity of the cosmetic substance to be sprayed is varied on the basis of an inclination of the device relative to a reference point, the reference point being a horizontal line, a vertical line or a point of reference at or on the person. In this case, it is expedient if the output quantity of the cosmetic substance to be sprayed is increased when the inclination of the device relative to the reference point becomes greater and if the output quantity of the cosmetic substance to be sprayed is decreased when the inclination of the device relative to the reference point becomes smaller.

In all three variants—whether individually or in combination—the skin of the person using the device always has the correct layer thickness of cosmetic substance applied to it. Said cosmetic substance may be a sunscreen, for example. The skin is always protected in optimum fashion with the correct sun protection factor.

In an advantageous development of the method according to the invention, the at least one sensor can capture the voltage at the high-voltage source of the device.

Preferably, there is provision for a separate sensor for each type of measured value, with multiple sensors, the measured values of which combine to produce one piece of information, also being able to be used for one measured value.

For capturing the further measured values, there may be provision for at least one further sensor so that the processor can take into consideration the further measured values when calculating the at least one result.

The at least one further sensor captures e.g. ambient temperature, relative humidity, air pressure, geographical height, the geographical position of the device, and the like.

The at least one further sensor may be accommodated in the device itself. However, it may also be assigned to the external data processing apparatus and installed there. In that case, the further measured values are transmitted from the external data processing apparatus to the processor by way of the transmitting and receiving unit of the device.

One development of the invention provides for the processor to take into consideration the personal data of the person when calculating the at least one result. This allows the method for applying the cosmetic substance to be personalized further and adapted for the individual needs of the person.

The personal data of the person are preferably input into the external data processing apparatus, e.g. a computer, a tablet or a smartphone, that is provided with appropriate software. However, the personal data can also be ascertained by the external data processing apparatus on the basis of a database, on the Internet, another data source, or the like.

The personal data of the person are transmitted from the external data processing apparatus to the processor by way of the transmitting and receiving unit of the device, as a result of which said processor can adapt or vary the output quantity of the cosmetic substance to be sprayed from the device when required.

The personal data of the person can relate for example to sex, age, height, weight, skin type, skin color, skin class, skin sensitivity, nationality, self-protection time (erythema time), and the like.

In yet another embodiment of the invention, the processor can also take into consideration the further external data when calculating the at least one result.

The further external data are input into the external data processing apparatus or ascertained by said external data processing apparatus on the basis of a database, on the Internet, another data source, or the like, and subsequently transmitted from the external data processing apparatus to the processor by way of the transmitting and receiving unit of the device.

The further external data can be the season, the time of day, the hour, the date, the country that the person is in, the geographical location that the person is at, the ambient temperature, the relative humidity, the air pressure, the geographical height, a UV index, the local UV exposure, and the like.

UV index values can be obtained from publicly available databases. However, the values can also be ascertained from a built-in UV sensor in the device.

In a further important embodiment of the method according to the invention, the processor compares the measured values, the further measured values, the personal data and/or the further external data with reference values when calculating the at least one result. Said reference values can be configured as limit values, for example, as a result of which specific parameters are not exceeded or fallen short of and the output quantity of cosmetic substance can be adapted accordingly.

The reference values are preferably filed in the memory.

However, the reference values can additionally or alternatively also be input into the external data processing apparatus or ascertained by said external data processing apparatus on the basis of a database, on the Internet, another data source, or the like.

The reference values are transmitted from the external data processing apparatus to the processor by way of the transmitting and receiving unit of the device.

In an advantageous variant of the method, a motion profile of the device and/or of the person carrying the device is ascertained from the measured values of the at least one sensor, the further measured values of the at least one further sensor, the personal data of the person, the further external data and/or the results ascertained by the processor.

This motion profile is preferably calculated by the processor. However, it can also be calculated by the external data processing apparatus and subsequently transmitted to the device and the processor.

Each motion profile is expediently assigned to a person or a group of people, the assignment being made on the basis of the personal data and/or on the basis of the external data.

Each motion profile or selected motion profiles and/or the assignment of a motion profile to a person are filed in the memory. However, the profiles can also be stored externally in the external data processing apparatus.

It is thus possible to identify a person, namely a user of the device, and to adjust or adapt the output quantity of the cosmetic substance accordingly.

An important development of the method according to the invention therefore provides for the currently ascertained or calculated motion profile to be compared with the stored motion profiles, and for the output quantity of the cosmetic substance to be sprayed from the device to be adapted or varied in the event of an at least partial match with a stored motion profile.

The comparison of the motion profiles is performed by the processor and/or by the external data processing apparatus, it being necessary to stipulate the degree to which or the range in which the ascertained motion profile needs to match a stored motion profile.

An advantageous development of the invention provides for information about the skin type and/or the skin profile of the person to be generated from the measured values, the further measured values, the personal data of the person, the further external data, the results calculated by the processor and/or the motion profile of the device.

There is thus not only the possibility of ascertaining and realizing the individually optimum output quantity for the cosmetic substance. Rather, there is the possibility of providing the person wishing to use the device with individual recommendations in regard to the selection of the cosmetic substance.

The person can input further information or details into the external data processing apparatus for the purpose of determining the skin type and/or the skin profile. To this end, said external data processing apparatus is provided with appropriate software or an appropriate app. The further information can also include images of the person, of the face of the person or of sections of the skin of the person, which are loaded into the external data processing apparatus.

The information and details from the person are analyzed and/or evaluated by the external data processing apparatus and processed to produce personal information.

Thus, not only individual adaptation of the output quantity of cosmetic substance is possible. The method can use the data processing apparatus or the device itself to deliver information to the person using or wishing to use the device. This information can relate to the cosmetic substance or to the way in which the device is used or to the frequency and the intervals of use of the device with the respective cosmetic substance.

A further embodiment of the invention provides for information about a sun protection factor suitable for the person to be generated from the measured values, the further measured values, the personal data of the person, the further external data, the results calculated by the processor and/or the motion profile of the device.

Yet another embodiment of the invention provides for information about a cosmetic substance suitable for the person to be generated from the measured values, the further measured values, the personal data of the person, the further external data, the results calculated by the processor and/or the motion profile of the device.

One development of the invention also provides for time information for the person to be generated from the measured values, the further measured values, the personal data of the person, the further external data, the results calculated by the processor and/or the motion profile of the device.

The device and/or the data processing apparatus can therefore remind the person who has used the device to renew or repeat application, as a result of which the cosmetic substance can always be applied in optimum fashion and work in optimum fashion.

The information about the skin type and/or the skin profile of the person, the personal information, the suitable sun protection factor, the suitable cosmetic substance and/or the time information are preferably determined by the processor and/or by the external data processing apparatus.

Particularly advantageously, the information about the skin type and/or the skin profile of the person, the personal information, the suitable sun protection factor, the suitable cosmetic substance and/or the time information are also transmitted from the external data processing apparatus to the processor by way of the transmitting and receiving unit of the device and are added to the personal data of the person and/or to the further external data.

As a result, the method according to the invention can make a self-learning diagnosis and always adapt the output quantity of the cosmetic substance in optimum fashion for the person using the device in each case. It is therefore an iteratively learning method.

Accordingly, a further advantageous design of the invention provides for the processor, while the device is being used, to take the information about the skin type and/or the skin profile of the person, the personal information, the suitable sun protection factor, the information about the suitable cosmetic substance and/or the time information as a basis for adapting or varying the output quantity of the cosmetic substance to be sprayed from the device.

In order to individualize, personalize and/or optimize the use and application of the cosmetic substance further, the method according to the invention provides for the person to have to input responses to questions into the external data processing apparatus after using the device.

The responses of the person are analyzed and/or evaluated by the external data processing apparatus and are processed to produce further personal information, wherein the further personal information is transmitted from the external data processing apparatus to the processor by way of the transmitting and receiving unit of the device and is added to the personal data of the person. The external data processing apparatus also has appropriate software or an appropriate app installed on it for this purpose.

A further design of the invention provides for the switching-on of the device to result in an AC pulse being generated and a signal reflected from the person being captured by a sensor or a further sensor.

This allows the device to be used by more than one person, for example within a family or among friends. As soon as a person picks up the device and switches it on, the AC pulse is triggered. The "echo" thereof is sent from the person back to the device, where it is captured by a suitable sensor. This information can be used to calculate a body volume, for example, which can be taken as a basis for identifying the person, possibly by using further personal data. As soon as the person has been recognized, use data can be automatically and correctly assigned, for example in order to reset a use alarm.

The device expediently has a housing that accommodates the container for the cosmetic substance, the nozzle arrangement for spraying the cosmetic substance, the conveying apparatus for conveying the cosmetic substance from the container to the nozzle arrangement, the high-voltage source, the processor for processing measured values, data and/or reference values, the memory for storing the measured values, data and/or reference values and the transmitting and receiving unit for transferring the measured values, data and/or reference values to an external data processing apparatus and/or for receiving further measured values, data and/or reference values from the external data processing apparatus.

The processor, the memory and/or the at least one further sensor may additionally or alternatively be accommodated in the external data processing apparatus. This would allow the device to be designed more compactly overall.

The external data processing apparatus is preferably a computer, a tablet, a smartphone, a console, or the like.

In yet another embodiment of the method according to the invention, the external data processing apparatus files the measured values, the further measured values, the personal data of the person, the further external data, the at least one result calculated by the processor and/or the motion profile of the device in a database. Said database may be stored in a cloud.

From these data, the method can detect that e.g. a large number of comparable people (e.g. with the same skin type, at the same location, under comparable UV exposure) have not applied sufficient cream. This information is then passed on as a learning function to the whole group of people, and the respective device is used according to the individual person, i.e. the optimum output quantity of cosmetic substance for the respective person is generated-taking into consideration the measured values, the further measured values, the personal data, the further external data and/or the reference values.

BRIEF DESCRIPTION OF THE DRAWINGS

Further features, details and advantages of the invention become apparent from the wording of the claims and from the description of exemplary embodiments that follows with reference to the drawings, in which:

FIG. 1 shows a schematic depiction of a device for performing the method according to the invention.

DETAILED DESCRIPTION

The device 10, which is depicted purely schematically in FIG. 1, is intended to apply a cosmetic substance S to the skin H of a person P (who is not depicted in more detail). The cosmetic substance S may be for example a skincare product, a lotion, a sunscreen, a self-tanning cream, an insect repellent, and the like. The person is a man, a woman, a child, regardless of age.

The device 10 is in the form of an electrostatic spraying device. In a housing 12, it has a container 20 for the cosmetic substance S, a nozzle arrangement 30 for spraying the cosmetic substance S, a conveying apparatus 40, for conveying the cosmetic substance S from the container 20 to the nozzle arrangement 30, and a high-voltage source 50. The container 20, the conveying apparatus 40 and the nozzle arrangement 30 have a hose system 22, 42 arranged between them. The high-voltage source 50 has one or more electrode(s) (not depicted in more detail) for the electrostatic atomization in the nozzle arrangement 30.

The housing also contains a processor 70 for processing measured values, data and/or reference values, a memory 80 for storing the measured values, data and/or reference values, and a transmitting and receiving unit 90 for transferring the measured values, data and/or reference values to an external data processing apparatus 100 and/or for receiving further measured values, data and/or reference values from the external data processing apparatus 100.

The external data processing apparatus is preferably a computer, a tablet, a smartphone, a console, or the like, that is connected to the transmitting and receiving unit 90 of the device 10 by way of a radio link 102.

The device 10 also has a power supply 55, for example a replaceable battery or a storage battery, the storage battery being able to be charged by way of an external charger (not shown) when required. The power supply 55 supplies the conveying apparatus 40, the high-voltage source 50 and the processor 70 with electric power.

At least one switch or pushbutton switch (not depicted) can be used to start up the device 10. Audible and/or visual signal generators, which are likewise not shown, provide information—when required—about the operating state of the device 10 and about the fill level in the container 20. If required, the device 10 may also be provided with a display (likewise not shown).

In one embodiment, the method according to the invention provides for the measured values to be captured and/or ascertained and transmitted to the processor 70. Subsequently, the processor 70 uses suitable software to process the measured values to produce at least one result. On the basis of this result, the processor 70 varies the output quantity of the cosmetic substance S to be sprayed from the device 10. The output quantity can be varied by virtue of the processor 70 regulating the conveying apparatus 40, for example by virtue of the conveying apparatus 40 conveying more or less of the cosmetic substance from the container 20 to the nozzle arrangement 30. Preferably, the conveying speed is regulated. However, the conveying volume can also be changed or adapted.

The processor 70 can-additionally or alternatively-vary the output quantity of the cosmetic substance S to be sprayed by regulating the high-voltage source 50, for example by virtue of the high voltage applied to the electrodes being altered.

It is also conceivable for the processor 70 to vary the output quantity of the cosmetic substance S to be sprayed by altering the nozzle arrangement 30. By way of example, the nozzle cross sections can be influenced or individual nozzles are engaged or disengaged. It is also conceivable to influence the spraying angle.

It is advantageous if the output quantity of the cosmetic substance S to be sprayed is varied on the basis of the results that the processor has calculated in real time. In this way, changes in the ascertained measured values are immediately taken into consideration and the output quantity is adapted accordingly, which has a beneficial effect on the distribution of the cosmetic substance on the skin H of the person P.

The device 10 may be designed such that, besides the measured values, further measured values, personal data of the person P, further external data and/or reference values are also taken into consideration when calculating the at least one result.

There may be provision in the device 10 for at least one sensor 60 for capturing measured values. Said sensor is employed by the method according to the invention such that the measured values are captured during application of the cosmetic substance S to the skin H of the person P.

By way of example, while the device 10 is being moved by the person P, the sensor 60 captures a speed. These measured values are transmitted to the processor 70 and evaluated. In this way, it is possible to vary the output quantity of the cosmetic substance S to be sprayed on the basis of the speed of the device 10, i.e. the output quantity is adapted for the movement of the device 10 by the person P. The output quantity can be increased by way of the processor 70 when the speed rises, whereas the output quantity of the cosmetic substance S to be sprayed is decreased when the speed falls.

The speed can be captured by way of a sensor 60. However, multiple sensors, preferably three sensors 60, can also be employed in order to be able to capture the speed of the device 10 in all three spatial directions. The ascertained measured values are forwarded to the processor 70, which processes the measured values and calculates motion data (results). On the basis of these motion data, the optimum spray quantity is calculated and the output quantity is varied accordingly, preferably in real time.

It is thus possible to generate a motion-dependent, variable output quantity of the cosmetic substance S to achieve a desired layer thickness.

In the case of sunscreens, for example, the correct protection for the respective person P firstly presupposes the correct UV filter content in the cosmetic substance S, and said correct UV filter content then secondly needs to be applied to the skin H in the correct layer thickness. Too little sun protection "dilutes" protection from the sun (example: a sunscreen having the sun protection factor SPF50, when applied too thinly, provides only the same protection as a sunscreen having the sun protection factor SPF30). On top of that, consumers apply on average 80 to 90% too little sunscreen to the skin, and so this also means that optimum protection from the sun is not ensured.

In the case of handheld devices, applying the correct layer thickness using a spraying device requires an exact combination of the speed of movement of the hand carrying the device and the output quantity. Current spraying devices have only a constant output quantity. As the speed of movement of the arm of the person P applying the sunscreen is always different, however, and also as the movement motor function of the person P during the spraying process is different, a constant output quantity leads to different layer thicknesses.

By contrast, the method according to the invention provides for the speed of movement of the device 10 to be captured by way of the installed sensors 60. The ascertained measured values are transmitted to the processor 70, which analyzes the measured values and calculates motion data. On the basis of these results, i.e. on the basis of the speed of movement of the device 10, the output quantity of the cosmetic substance S is varied, as a result of which the optimum quantity of substance S is always applied in each section of the skin H of the person P. The output quantity can be varied by virtue of the processor 70 being used to regulate and/or alter the conveying apparatus 40, the high-voltage source 50 and/or the nozzle arrangement 30.

In an alternative or additional refinement of the method, the output quantity of the cosmetic substance S to be sprayed is varied on the basis of an acceleration and/or a deceleration of the device 10. By way of example, the output quantity is increased for an acceleration of the device 10, whereas the output quantity is decreased for a deceleration of the device 10.

It is also possible to vary the output quantity of the cosmetic substance S to be sprayed on the basis of an inclination of the device 10 relative to a reference point, the reference point being a horizontal line, a vertical line or a point of reference at or on the person P. By way of example, it is expedient if the output quantity is increased when the inclination of the device 10 relative to the reference point becomes greater, whereas the output quantity is decreased when the inclination of the device 10 relative to the reference point becomes smaller.

As the skin H of people P is individually different and the geographical location of consumers may be different, the ideal values for a sun protection factor also differ from consumer to consumer. Given fixed, specific sun protection factors, the protection for any user is thus sufficient only to different degrees.

The method according to the invention provides the opportunity to use the variation of the output quantity and hence of the layer thickness of the cosmetic substance S to individually adapt application for a wide variety of people P by virtue of further measured values, personal data of the person P, further external data and/or reference values being captured and/or ascertained and transmitted to the processor 70.

This allows the e.g. actually applied sun protection factor of a sunscreen to be controlled in personalized fashion, for example by virtue of too little of a sunscreen having the sun protection factor 50 deliberately being applied, i.e. the sun protection factor 50 is "diluted" to 30.

The person-individual, ideal output quantity can therefore be determined by way of the learnt personal diagnosis data and by way of the target layer thickness. However, it is thus possible for e.g. only a single type of sunscreen to be kept in the device, which sunscreen is used for a wide variety of people P. By way of example, the device 10 is filled with a sunscreen having the sun protection factor 50. The method according to the invention can be used to "stretch" this substance S to different sun protection factors and thus render it open to mass personalization.

For capturing the further measured values, there can be provision for at least one further sensor 66 so that the processor 70 can take into consideration the further measured values when calculating the at least one result.

The at least one further sensor 66 captures e.g. ambient temperature, relative humidity, air pressure, geographical height, the geographical position of the device 10, and the like.

The at least one further sensor may be accommodated in the device 10 itself. However, it may also be assigned to the external data processing apparatus 100 and installed there. In that case, the further measured values are transmitted from the external data processing apparatus 100 to the processor 70 by way of the transmitting and receiving unit 90 of the device 10.

The processor 70 can also take into consideration the personal data of the person P when calculating the at least one result. Said personal data are preferably input into the external data processing apparatus 100, e.g. a computer, a tablet or a smartphone, which is provided with appropriate software and is connected to the device 10 by way of the radio link 102. However, the personal data can also be ascertained by the external data processing apparatus 100 on the basis of a database, on the Internet, another data source, or the like.

The personal data of the person are transmitted from the external data processing apparatus 100 to the processor 70 by way of the transmitting and receiving unit 90 of the device 10, as a result of which said processor can adapt or vary the output quantity of the cosmetic substance S to be sprayed from the device 10 when required.

The personal data of the person relate for example to sex, age, height, weight, skin type, skin color, skin class, skin sensitivity, nationality, self-protection time (erythema time), and the like.

Further adaptations of the method, further individualizations for the person P using the device 10 and hence even more accurate adaptation and personalization of the output quantity are achieved if the processor 70 takes into consideration the further external data when calculating the at least one result.

The further external data are preferably input into the external data processing apparatus 100 or ascertained by said external data processing apparatus on the basis of a database, on the Internet, another data source, or the like. Subsequently, the data are transmitted from the external data processing apparatus 100 to the processor 72 by way of the transmitting and receiving unit 90 of the device 10.

The further external data can be the season, the time of day, the hour, the date, the country that the person is in, the geographical location that the person is at, the ambient temperature, the relative humidity, the air pressure, the geographical height, a UV index, the local UV exposure, and the like.

For further individualization and optimization of the output quantity of cosmetic substance S from the device 10 during use by a person P, the processor 70 can compare the measured values, the further measured values, the personal data and/or the further external data with reference values when calculating the at least one result.

These reference values are preferably limit values that limit the one or other parameter at the top and/or bottom, as a result of which the predefined value is not exceeded or fallen short of. In this way, it is possible for example to define temperature ranges or times of day in order to be able to adapt the output quantity of cosmetic substance S accordingly.

The reference values are preferably filed in the memory. However, they can also be input into the external data processing apparatus 100 or ascertained by said external data processing apparatus on the basis of a database, on the Internet, another data source, or the like. Following stipulation of the reference values, said reference values are transmitted from the external data processing apparatus 100 to the device 10 or to the processor 70 by way of the transmitting and receiving unit 90.

The design of the method according the invention allows a wide variety of applications to be realized.

For example, it is possible to identify a user, i.e. a person P, and to adapt or vary the output quantity of the device 10 according to the recognized person.

This is necessary if the device 10 is used by more than one person P (e.g. within a family, a group or among friends). Consequently, the task of automatically correctly assigning the use data to the individual user P arises, for example in order to adapt the output quantity, to trigger a time alarm for repeated application of the cosmetic substance S—for example a sunscreen—or in order to issue reminders about changing the container and hence the substance S. Manual assignment of the use data (for example before the spraying process or afterwards) would be impractical and would often be forgotten anyway.

In an advantageous variant of the method, a motion profile of the device 10 and/or of the person P carrying the device 10 is therefore ascertained from the measured values of the at least one sensor 60, the further measured values of the at least one further sensor 66, the personal data of the person, the further external data and/or the results ascertained by the processor. This motion profile is preferably calculated by the processor 70. However, it can also be calculated by the external data processing apparatus 100 and subsequently transmitted to the device 10 and the processor 70.

Each motion profile is expediently assigned to a person P or a group of people, the assignment being made on the basis of the personal data and/or on the basis of the external data.

The device 10 is thus capable, for example during a process of applying cream, of capturing and identifying the unique movement motor function of a person P in the manner of a fingerprint. If e.g. two people P are of different height, then the device 10 covers a different distance in space for each of these people during spraying. Furthermore, the device is held differently, i.e. the acceleration and the inclination may also be different. Each person thus runs down the body with the device 10 when spraying, the movement following the contours of the body. By capturing this motion profile (by way of speeds, inclinations and accelerations), a body shape can be detected, which then allows the identification of a person. The more frequently a person P sprays, the more accurately the device detects the body shape and the motor function profile, as a result of which invariably reliable user recognition is possible after the device 10 has been "trained".

This also permits use data to be automatically assigned to an identified user as soon as said user moves the device 10 or has input or retrieved his personal data.

Each motion profile or selected motion profiles and/or the assignment of a motion profile to a person are filed in the memory 80. However, the profiles can also be stored externally in the external data processing apparatus 100. In this way, the motion profiles can be compared, i.e. when a person begins to spray, the processor 70 can recognize the person.

In a further refinement, the device 10 can trigger an AC pulse as soon as the person P picks up the device 10 and switches it on. The signal reflected from the person allows a body volume to be calculated. If two people P have different heights and weights, the echo will also generate different signals. These signals can then be used by the device 10 to distinguish between the people P.

The method according to the invention also allows the performance of diagnoses and the individual recommendation of a cosmetic substance S, for example in regard to the selection of a sunscreen having a specific sun protection factor. End users often do not know which sun protection factor is ideal for them. Typically, they take the next best sun protection factor, or always the same, familiar sun protection factor. Incidences of sunburn indicate that end users make mistakes here during selection.

Correct selection of the sun protection factor incorporates various parameters.

First, the specific UV exposure in situ must be incorporated. The end user can certainly find out the UV exposure from public facilities (also via smartphone). These are usually very inaccurate, however, because the UV index is not ascertained over a wide area (in Germany e.g. only once per federal state).

A further parameter needing to be taken into consideration is the extremely individual self-protection time or erythema time of the individual skin. The self-protection time can be estimated by the end user by assigning himself to one of five skin type classes by way of inspection. These skin types are an extreme simplification, however, and in any case do not permit abnormal self-protection times (e.g. dark skin, but high skin sensitivity). At the same time, it must be assumed that the actual UV exposure and the self-protection time do not have a linear relationship.

Finally, sun protection factor itself is only an approximate value. For the purpose of formulation, it is ascertained using standard methods by determining the sunburn time with sun protection in a defined number of subjects. The results are then weighted and converted into a value for the sun protection factor. The averaging alone and general difficulties in homogeneous application mean that this value is thus by no means accurate.

The method according to the invention provides a remedy here.

As a result of the further measured values, the personal data of the person P, the further external data and/or the reference values being taken into consideration and input, the device 10 can be used to perform individual determination of the individual skin profile, preferably on the external data processing apparatus 100 and using software (an app) installed thereon.

Before the device 10 is used, for example, this software can ask questions that the person P needs to answer. The questions can be supplemented by an image of the person, e.g. by a photograph of the face or of selected sensitive areas of skin. The software analyzes the input responses and images and creates personal data therefrom that are subsequently transmitted from the external data processing apparatus 100 to the device 10 and hence to the processor 70 by way of the transmitting and receiving unit 90.

The personal data can be supplemented by the obtainment of UV index values, for example from publicly available data or from a UV sensor (not shown) integrated in the device 10.

The processor processes all measured values, further measured values, personal data and external data and calculates a result, which is used for recommending an ideal value for the sun protection factor. This value can be displayed by the device itself or by the external data processing apparatus 100.

The processor can also take the measured values, the further measured values, the personal data of the person and the further external data as a basis for generating information about the skin type and/or the skin profile of the person P, and on that basis can vary the output quantity of the cosmetic substance S accordingly.

There is thus not only the possibility of ascertaining and realizing the individually optimum output quantity for the cosmetic substance S. Rather, there is the possibility of providing the person P wishing to use the device 10 with individual recommendations in regard to the selection of the cosmetic substance S. Time windows in which the substance S should ideally be applied can be predefined. Reminder signals can be generated to remind the person P to reapply the substance S.

In a further refinement of the method according to the invention, the device 10 can make a self-learning diagnosis and always adapt the output quantity of the cosmetic substance S in optimum fashion for the person P using the device 10 in each case. It is therefore an iteratively learning method.

Another variant provides for the processor 70, while the device 10 is being used, to take the information about the skin type and/or the skin profile of the person P, the personal information, the suitable sun protection factor, the information about the suitable cosmetic substance S and/or the time information as a basis for adapting or varying the output quantity of the cosmetic substance to be sprayed from the device.

The device 10 can thus take the available measured values, information and data as a basis for reminding the person P at the correct time that he needs to apply cream, when he needs to put on sunglasses, when he needs to get out of the sun completely, and the like.

In a further modification, the device 10 can also issue reminders about when the person P needs to reapply the cosmetic substance, for example because protection from the sun typically deteriorates as a result of movement and bathing. The exact time of the sun protection alarm is determined by the measured values, information and data that have been transmitted to the device 10 or to the processor 70. As such, the personal information can also comprise data about a motion profile (in the case of sports activity) or further personal data (e.g. sweating behavior).

In this way, the device 10 uses the method according to the invention to ensure that sunburn is effectively avoided. The device ensures that the person always uses the correct sun protection factor and above all applies the correct quantity of cosmetic substance S at the correct time. The motion profiles can additionally be used to identify whether one or other area of skin may not have had cream applied sufficiently or at all.

In order to individualize, personalize and/or optimize the use and application of the cosmetic substance S further, the method according to the invention provides for the person P to have to input responses to questions into the external data processing apparatus 100 after using the device 10.

The responses of the person are analyzed and/or evaluated by the external data processing apparatus 100 and are processed to produce further personal information, wherein the further personal information is transmitted from the external data processing apparatus 100 to the processor by way of the transmitting and receiving unit 90 of the device 10 and is added to the personal data of the person.

In yet another embodiment of the method according to the invention, the external data processing apparatus files the measured values, the further measured values, the personal data of the person, the further external data, the at least one result calculated by the processor and/or the motion profile of the device in a database. Said database may be stored in a cloud.

From these data, the method can detect that e.g. a large number of comparable people (e.g. with the same skin type, at the same location, under comparable UV exposure) have not applied sufficient cream. This information is then passed on as a learning function to the whole group of people, and the respective device is used according to the individual person, i.e. the optimum output quantity of cosmetic substance for the respective person is generated-taking into consideration the measured values, the further measured values, the personal data, the further external data and/or the reference values.

Capture of these use data for all devices 10 can be used to identify user groups and to derive recommendations for the individual user from the behavior of similar user groups.

The invention is not restricted to one of the embodiments described above, but rather can be modified in a wide variety of ways.

As such, two or three sensors can also be used for capturing the acceleration and inclination of the device 10.

Preferably, there is provision for a separate sensor for each type of measured value, with multiple sensors, the measured values of which combine to produce one piece of information, also being able to be used for one measured value.

In one development of the method according to the invention, the at least one sensor can capture the voltage at the high-voltage source of the device and can forward this information to the processor.

It is also conceivable for visual or audible signal generators to be used directly in the device that display a cosmetic substance to be used, issue reminders about application of the substance or provide the person using the device with other information.

It can be seen that the invention relates to a method for applying a cosmetic substance S to the skin H of a person P, using a device 10 for electrostatically spraying the cosmetic substance S. The device 10 has a container 20, a nozzle arrangement 30, a conveying apparatus 40, a high-voltage source 50, a processor 70 for processing measured values, data and/or reference values, a memory 80 and a transmitting and receiving unit 90 for transferring the measured values, data and/or reference values to an external data processing apparatus 100 and/or for receiving further measured values, data and/or reference values from the external data processing apparatus 100. The method provides for the measured values and possibly further measured values, personal data of the person P, further external data and/or reference values to be captured and/or ascertained and transmitted to the processor 70, wherein the processor 70 processes the measured values, the further measured values, the personal data, the further external data and/or the reference values to produce at least one result and takes these results as a basis for varying the output quantity of the cosmetic substance S to be sprayed from the device 10.

All features and advantages emerging from the claims, the description and the drawing, including structural details, spatial arrangements and method steps, may be essential to the invention both by themselves and in a wide variety of combinations.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method for applying a cosmetic substance to a skin of a person, using a device for electrostatically spraying the cosmetic substance, the device comprising:
    a container for the cosmetic substance,
    a nozzle arrangement for spraying the cosmetic substance,
    a conveying apparatus, for conveying the cosmetic substance from the container to the nozzle arrangement,
    a high-voltage source,
    a processor for processing measured values, data and/or reference values,
    a memory for storing the measured values, the data and/or the reference values,
    a transmitting and receiving unit for transferring the measured values, the data and/or the reference values to an external data processing apparatus and/or for receiving further the measured values, the data and/or the reference values from the external data processing apparatus,
    the method comprises:
    a) the measured values, further measured values, personal data of the person, further external data and/or the reference values are captured and/or ascertained and transmitted to the processor, wherein the further measured values include a voltage, a current, an electrical resistance, or a combination thereof between the device and the person;
    b) the processor stores the further measured values on the memory and assigns the further measured values to the person;
    c) the processor compares the further measured values to stored values and/or processes the measured values, the further measured values, the personal data, the further external data and/or the reference values to produce at least one result;
    d) the processor produces a same result if at least one of the further measured values is same as and/or within a predetermined margin of error as one of the stored values; and
    e) the processor takes the at least one result as a basis for varying an output quantity of the cosmetic substance to be sprayed from the device by regulating the conveying apparatus and/or by regulating the high-voltage source.

2. The method as claimed in claim 1, wherein the processor varies the output quantity of the cosmetic substance to be sprayed by influencing the nozzle arrangement.

3. The method as claimed in claim 1, wherein the output quantity of the cosmetic substance to be sprayed is varied on the basis of the at least one result in real time.

4. The method as claimed in claim 1, wherein the device comprises at least one sensor, wherein the measured values are captured by the at least one sensor during application of the cosmetic substance to the skin of the person.

5. The method as claimed in claim 4, wherein the at least one sensor captures a speed, an acceleration, a deceleration, and/or an inclination of the device.

6. The method as claimed in claim 4, wherein the at least one sensor captures a voltage at the high-voltage source of the device.

7. The method as claimed in claim 4, wherein at least one further sensor captures the further measured values.

8. The method as claimed in claim 7, wherein a motion profile of the device and/or of the person is ascertained from the measured values of the at least one sensor, the further measured values of the at least one further sensor, the personal data of the person, the further external data and/or the at least one result ascertained by the processor, each motion profile being assigned to the person.

9. The method as claimed in claim 7, wherein the processor takes into consideration the further measured values when calculating the at least one result.

10. The method as claimed in claim 1, wherein the processor takes into consideration the personal data of the person when calculating the at least one result.

11. The method as claimed in claim 10, wherein the personal data of the person are input into the external data processing apparatus and/or ascertained by said external data processing apparatus on the basis of a database, on the Internet, or another data source.

12. The method as claimed in claim 1, wherein the processor takes into consideration the further external data when calculating the at least one result.

13. The method as claimed in claim 12, wherein the further external data are input into the external data processing apparatus and ascertained by said external data processing apparatus on the basis of a database, on the Internet, or another data source.

14. The method as claimed in claim 1, wherein the processor compares the measured values, the further measured values, the personal data and/or the further external data with the reference values when calculating the at least one result.

15. The method as claimed in claim 14, wherein a currently ascertained or calculated motion profile is compared with a stored motion profile, wherein the output quantity of the cosmetic substance to be sprayed from the device is adapted or varied in an event of an at least partial match with the stored motion profile.

16. The method as claimed in claim 15, wherein information about a skin type and/or a skin profile of the person is generated from the measured values, the further measured values, the personal data of the person, the further external data, the at least one result calculated by the processor and/or a motion profile of the device.

17. The method as claimed in claim 16, wherein information about a sun protection factor suitable for the person is generated from the measured values, the further measured values, the personal data of the person, the further external data, the at least one result calculated by the processor and/or the motion profile of the device.

18. The method as claimed in claim 16, wherein information about the cosmetic substance suitable for the person is generated from the measured values, the further measured values, the personal data of the person, the further external data, the at least one result calculated by the processor and/or the motion profile of the device.

19. The method as claimed in claim 16, wherein time information for the person is generated from the measured values, the further measured values, the personal data of the person, the further external data, the at least one result calculated by the processor and/or the motion profile of the device.

20. The method as claimed in claim 19, wherein the information about the skin type and/or the skin profile of the person, personal information, a suitable sun protection factor, a suitable cosmetic substance and/or the time information are transmitted from the external data processing apparatus to the processor by way of the transmitting and receiving unit of the device and are added to the personal data of the person and/or to the further external data.

21. The method of claim 1, wherein the processor varies the output quantity of the cosmetic substance to be sprayed by regulating the conveying apparatus.

22. The method of claim 1, wherein the processor varies the output quantity of the cosmetic substance to be sprayed by regulating the high-voltage source.

23. A device for applying a cosmetic substance to a skin of a person, comprising:
a container for the cosmetic substance;
a nozzle arrangement for spraying the cosmetic substance;
a conveying apparatus for conveying the cosmetic substance from the container to the nozzle arrangement;
a high-voltage source;
at least one sensor for acquiring measured values while applying the cosmetic substance to the skin of the person;
a processor for processing the measured values, data, and/or reference values to produce at least one result, wherein the data comprises further measured values, further personal data relating to the person, further external data, and further reference values;
a memory for storing the measured values, the data, and/or the reference values;
a transmitting and receiving unit for transferring the measured values, the data, and/or the reference values to an external data processing apparatus from the at least one sensor to the processor and/or for receiving the further measured values, the data, and/or the reference values from the external data processing apparatus;
wherein the transmitting and receiving unit captures and/or ascertains and transmits to the processor the measured values, the further measured values, the further personal data relating to the person, and/or the further external data;
wherein the processor compares the measured values, the further measured values, the further personal data, and/or the further external data with the reference values when producing the at least one result;
wherein the processor takes the at least one result as a basis for varying an application rate of the cosmetic substance to be sprayed from the device.

24. The device of claim 23, wherein the at least one sensor captures the further measured values.

25. The device of claim 23, wherein the at least one sensor captures a speed, an acceleration, a deceleration, and/or an inclination of the device.

26. The device of claim 23, wherein the at least one sensor captures a voltage, a current, and/or an electrical resistance between the device and the person.

* * * * *